US006344575B1

(12) United States Patent
Rubin

(10) Patent No.: US 6,344,575 B1
(45) Date of Patent: Feb. 5, 2002

(54) EXTRACTION OF VOLATILE OILS

(75) Inventor: Ian Rubin, Leicestershire (GB)

(73) Assignee: Phytopharm PIC, Cambridgeshire (GB)

( * ) Notice: Subject to any disclaimer, the term of this patent is extended or adjusted under 35 U.S.C. 154(b) by 0 days.

(21) Appl. No.: 09/647,992

(22) PCT Filed: Feb. 10, 2000

(86) PCT No.: PCT/GB00/00419

§ 371 Date: Feb. 27, 2001

§ 102(e) Date: Feb. 27, 2001

(87) PCT Pub. No.: WO00/47703

PCT Pub. Date: Aug. 17, 2000

(30) Foreign Application Priority Data

Feb. 10, 1999 (GB) ............................................ 9903034

(51) Int. Cl.[7] ................................................ C07C 1/00

(52) U.S. Cl. ............................... 554/23; 554/8; 554/20

(58) Field of Search ................................ 554/8, 20, 23

(56) References Cited

FOREIGN PATENT DOCUMENTS

| | | |
|---|---|---|
| FR | 1 055 076 | 2/1954 |
| GB | 1 600 942 | 10/1981 |
| WO | 87 04710 | 8/1987 |
| WO | 99 35116 | 7/1999 |
| WO | 99 38392 | 8/1999 |

OTHER PUBLICATIONS

Choudhury et al., "Essential Oil of *Curcuma amada* Roxb. from Northeastern India", *J. Essent. Oil Res.*, (1996), vol. 8, pp. 79–80.

McCarron et al., "Carparison of the Monoterpenes Derived from Green Leaves and Fresh Rhizomes of *Curcuma longa* L. from India", *Flavor and Fragrance Journal*, (1995), vol. 10, pp. 355–357.

*Primary Examiner*—Deborah D. Carr

(74) *Attorney, Agent, or Firm*—Browdy and Neimark

(57) ABSTRACT

The invention relates to the process of extraction of volatile oils from plant material, such as turmeric (Curcuma spp.), comprising: subjecting freshly collected plant material to mechanical working, boiling the worked plant material, collecting the distillate and separating the components.

7 Claims, No Drawings

EXTRACTION OF VOLATILE OILS

This application is a 371 of PCT/GB00/00419 filed Feb. 10, 2000.

This invention relates to the extraction of volatile oils from plant material and is particularly (though not exclusively) concerned with the extraction of volatile oils from turmeric (Curcuma spp.).

The extraction of volatile oils from turmeric and other plant materials is usually undertaken using steam distillation. It is conventional, for most plant materials, to steam distil the plant material after it has been dried, which may involve natural drying in the sun or may be some form of oven drying.

Fresh material is not traditionally steam distilled for a number of reasons. These include the fact that capacity limitations may mean that a crop of fresh material cannot be distilled before it has spoiled or rotted. Other reasons why the fresh material is not steam distilled include the difficulties experienced in steam distillation of a wet vegetable mass, e.g. tracking of the steam through the bed of plane material and the tendency of the vegetable material to form an amorphous mass of plant material.

In the case of Curcuma, it has hitherto been assumed that it is not possible to extract the curcuminoids from the dry plant residue after the material has been distilled wet.

The process used hitherto for extracting volatile oils has thus been based on the traditional first step of drying the harvested plant material; and the stages of the overall process, starting with turmeric and including the additional step of extracting curcuminoids, are thus:

(1) dry the harvested plant material;

(2) steam distil the dried plant material;

(3) separate the condensed oils from the aqueous layer;

(4) dry the residue from step (2);

(5) subject the dried residue from step (4) to solvent extraction; and (6) remove solvent to produce the required curcuminoids.

The solvents employed in step (5) above were generally ethanol or acetone or a combination of alcohol and ketone solvents to extract the curcuminoids.

A further limitation of steam distillation of a large mass of plant material is that the process is very energy-inefficient. If one calculates the energy required to distil off the volatile oils and compares this to the energy used to achieve this end, then it is apparent that the process, in most steam distillation units, is very inefficient, with only a few percent of the input energy being required to volatilise the oils, the rest going to waste. The energy waste is compounded by the fact that cooling is required to condense the oils after distillation and the steam stream is also condensed in the process. The general inefficiency of the process is further manifest by the long cycle times to achieve a reasonable yield. For Curcuma this may typically be between 16 hours and 20 hours.

Furthermore, we have observed that the effect of the initial drying process is to reduce significantly the yield of the oils and other components that are sought from the production process.

Experiments have been conducted to assess the effects of different methods of distillation using both wet and dry plant raw material. These experiments produced surprising results. It was found that if fresh rhizomes were distilled a significantly greater yield of volatile oils could be obtained compared to the dried raw material distilled under equivalent conditions. What was also surprising was the finding that the rate at which the oil could be distilled off could be considerably increased when wet material was used in the steam distillation process as compared to the use of dried material. In addition there was no significant difference in the composition of the volatile oils that were obtained. Thus although considerable increases in the yield of the process and the efficiency of the process were achieved, there was no material change to the quality of the oils produced.

The efficiency of injecting live steam into a bad of plant material was compared to the efficiency of the distillation process when the plant materials were boiled in a minimal volume of water. For both the fresh and the dried plant raw materials the latter approach proved to be the most efficient in terms of both the total yield of oils and the rate of oil production. What was of significance was the finding that the mark (i.e. spent plant material) recovered after the steam distillation process had been completed could be successfully dried and the curcuminoids extracted using a solvent extraction process.

Additional experiments were conducted to investigate the effects of reducing the rate of energy input into the distillation process using a process where the plant raw material was boiled in water. Surprisingly it was found that the rate of oil production was not reduced when the energy input into the system was reduced. It was further discovered that reductions of the energy input could be achieved whilst maintaining the rate of oil production provided that the system was adequately stirred to ensure adequate heat transfer and to minimise the diffusion pathway for the oils.

According to the present invention, there is provided a process for extracting volatile oils from plant material, which comprises:

(1) subjecting freshly collected plant material to mechanical working to break down its physical structure;

(2) boiling the mechanically worked plant material in water and collecting the distillate; and (3) separating the components of the distillate to harvest the required volatile oils.

It will be appreciated that the fresh plant material is not subjected to any drying process before it is mechanically worked. It may, of course, be drained to remove any water adhering to the surface of the plant material.

Energy inputs are preferably minimised or at least ameliorated by reducing heat losses during the process using means which, per se, are conventional. For example, heat transfer during step (2) may be optimised by stirring. The rate of heat input can be adjusted so as to result in the production of the minimal quantities of steam.

Advantageously, the ratio by volume of plant material to water, during step (2), is in the range 1:0.5 to 1:3. This makes it possible to increase the ratio of oil to water in the distillate from less than 5% to a preferred ratio of 20 to 40%.

The mechanical working step advantageously involves grinding of the fresh plant material, but may additionally or alternatively involve one or more of: cutting, chopping, threshing, flailing, compressing, tearing or other comminution process. The comminution process selected will depend inter alia on the volume of fresh plant material to be processed and the availability of powered machinery. Traditional methods, e.g. grinding between mill stones, may be used where the plant material is collected and processed in tropical locations.

The separation of the volatile oils from the condensed distillate may, for example, be effected by decanting the supernatant oils from the aqueous layer (the two being immiscible). The process of the invention advantageously further comprises the steps of:

(4) collecting and drying the spent plant residue from step (2);

(5) subjecting the dried residue from step (4) to solvent extraction; and (6) removing the solvent to produce the required curcuminoids.

What is claimed is:

1. A process for extracting volatile oils from plant material, which comprises:

(1) subjecting freshly collected plant material to mechanical working to break down its physical structure;

(2) boiling the mechanically worked plant material in water and collecting the distillate; and (3) separating the components of the distillate to harvest the required volatile oils, wherein the ratio by volume of plant material to water, during step (2), is in the range 1:0.5 to 1:3.

2. A process according to claim 1, wherein said mechanical working step comprises grinding of the fresh plant material.

3. A process according to claim 1, wherein said mechanical working step comprises one or more of: cutting, chopping, threshing, flailing, compressing and tearing.

4. A process according to claim 1, wherein the separation of the volatile oils from the condensed distillate is effected by decanting the supernatant oils from the aqueous layer.

5. A process according to claim 1, which further comprises the steps of:

(4) collecting and drying the spent plant residue from step (2):

(5) subjecting the dried residue from step (4) to solvent extraction; and (6) removing the solvent to produce the required curcuminoids.

6. A process according to claim 1, wherein heat transfer is aided, during step (2), by stirring the mix of plant material and boiling water.

7. Volatile oils from plant material obtainable by process according to claim 1.

* * * * *